(12) United States Patent
Carroux

(10) Patent No.: US 9,339,283 B2
(45) Date of Patent: May 17, 2016

(54) URETERAL CALCULUS SUCTION INSTRUMENT HAVING A SHAFT

(75) Inventor: Alexander Carroux, Waltham, MA (US)

(73) Assignee: Olympus Winter IBE GmbH (DE)

(*) Notice: Subject to any disclaimer, the term of this patent is extended or adjusted under 35 U.S.C. 154(b) by 732 days.

(21) Appl. No.: 13/805,284

(22) PCT Filed: May 18, 2011

(86) PCT No.: PCT/EP2011/002465
§ 371 (c)(1),
(2), (4) Date: May 20, 2013

(87) PCT Pub. No.: WO2011/157338
PCT Pub. Date: Dec. 22, 2011

(65) Prior Publication Data
US 2013/0231677 A1    Sep. 5, 2013

(30) Foreign Application Priority Data

Jun. 18, 2010 (DE) .......................... 10 2010 024 360

(51) Int. Cl.
*A61B 17/22* (2006.01)
*A61B 1/015* (2006.01)
(Continued)

(52) U.S. Cl.
CPC .................. *A61B 17/22* (2013.01); *A61B 1/015* (2013.01); *A61B 1/307* (2013.01); *A61B 17/221* (2013.01); *A61B 17/3207* (2013.01); *A61M 1/008* (2013.01); *A61B 1/00087* (2013.01);
(Continued)

(58) Field of Classification Search
CPC .. A61B 17/22; A61B 17/221; A61B 17/3207; A61B 1/307; A61B 1/015; A61B 2017/22079; A61B 2018/00547; A61B 19/5212; A61B 2017/00287; A61B 2017/0023; A61B 2017/00274; A61B 2017/2215; A61B 2217/005; A61B 17/8822; A61B 2017/00353; A61M 1/008; A61M 1/0001; A61M 1/0058; A61F 2002/4685; A61F 2/4675
USPC .......................................................... 606/127
See application file for complete search history.

(56) References Cited

U.S. PATENT DOCUMENTS 3,050,062 A * 8/1962 Ulmer ................. A61M 1/0001
604/76
3,556,101 A * 1/1971 Economou .......... A61M 1/0017
604/319

(Continued)

FOREIGN PATENT DOCUMENTS

DE        82 535 A1    6/1971
DE     27 29 566 C3    1/1979

(Continued)

OTHER PUBLICATIONS

Translation of DE3542667.*

(Continued)

*Primary Examiner* — Amy R Weisberg
(74) *Attorney, Agent, or Firm* — Scully, Scott, Murphy & Presser, P.C.

(57) ABSTRACT

A ureteral calculus suction instrument having a shaft through which a suction channel that can be connected to a suction device passes, wherein a collecting container having a distal opening and a proximal opening is arranged distally from the shaft, of which openings the proximal opening is connected to the distal end of the suction channel.

13 Claims, 1 Drawing Sheet

(51) Int. Cl.
*A61B 1/307* (2006.01)
*A61B 17/221* (2006.01)
*A61B 17/3207* (2006.01)
*A61M 1/00* (2006.01)
*A61B 1/00* (2006.01)
*A61B 17/00* (2006.01)
*A61B 18/00* (2006.01)

(52) U.S. Cl.
CPC ............... *A61B2017/0023* (2013.01); *A61B 2017/00274* (2013.01); *A61B 2017/00287* (2013.01); *A61B 2017/2215* (2013.01); *A61B 2017/22079* (2013.01); *A61B 2018/00547* (2013.01); *A61B 2217/005* (2013.01)

(56) References Cited

U.S. PATENT DOCUMENTS

| | | | | | |
|---|---|---|---|---|---|
| 4,501,581 | A | * | 2/1985 | Kurtz | A61M 1/0001 604/4.01 |
| 4,873,978 | A | * | 10/1989 | Ginsburg | A61F 2/013 606/198 |
| 4,997,435 | A | * | 3/1991 | Demeter | A61B 17/22 604/104 |
| 5,029,580 | A | * | 7/1991 | Radford | A61M 1/0084 128/202.16 |
| 5,102,415 | A | * | 4/1992 | Guenther | A61B 17/22 604/103.05 |
| 5,125,893 | A | * | 6/1992 | Dryden | A61M 16/0463 128/207.14 |
| 5,181,908 | A | * | 1/1993 | Bell | A61M 16/0463 604/147 |
| 5,423,830 | A | * | 6/1995 | Schneebaum | A61B 18/10 606/110 |
| 5,458,138 | A | * | 10/1995 | Gajo | A61M 1/0001 128/205.12 |
| 5,820,373 | A | * | 10/1998 | Okano | A61C 17/02 433/216 |
| 6,159,230 | A | * | 12/2000 | Samuels | A61B 17/22031 606/200 |
| 8,435,237 | B2 | * | 5/2013 | Bahney | A61B 17/32056 606/113 |
| 2005/0049619 | A1 | | 3/2005 | Sepetka et al. | |
| 2006/0047286 | A1 | * | 3/2006 | West | A61B 17/221 606/114 |
| 2006/0155305 | A1 | * | 7/2006 | Freudenthal | A61B 17/221 606/114 |
| 2010/0022970 | A1 | * | 1/2010 | Hirszowicz | A61B 17/22032 604/268 |
| 2011/0213297 | A1 | * | 9/2011 | Aklog | A61B 17/22 604/28 |
| 2012/0232525 | A1 | * | 9/2012 | Golagani | A61M 1/0047 604/514 |
| 2013/0304082 | A1 | * | 11/2013 | Aklog | A61B 17/22 606/127 |
| 2015/0005781 | A1 | * | 1/2015 | Lund-Clausen | A61B 17/221 606/127 |
| 2015/0238207 | A1 | * | 8/2015 | Cox | A61B 17/221 606/159 |

FOREIGN PATENT DOCUMENTS

| | | |
|---|---|---|
| DE | 35 42 667 A1 | 6/1986 |
| DE | 43 35 783 A1 | 4/1995 |
| WO | WO 2010/019776 A2 | 2/2010 |

OTHER PUBLICATIONS

International Search Report dated Sep. 29, 2011 issued in PCT/EP2011/002465.

* cited by examiner

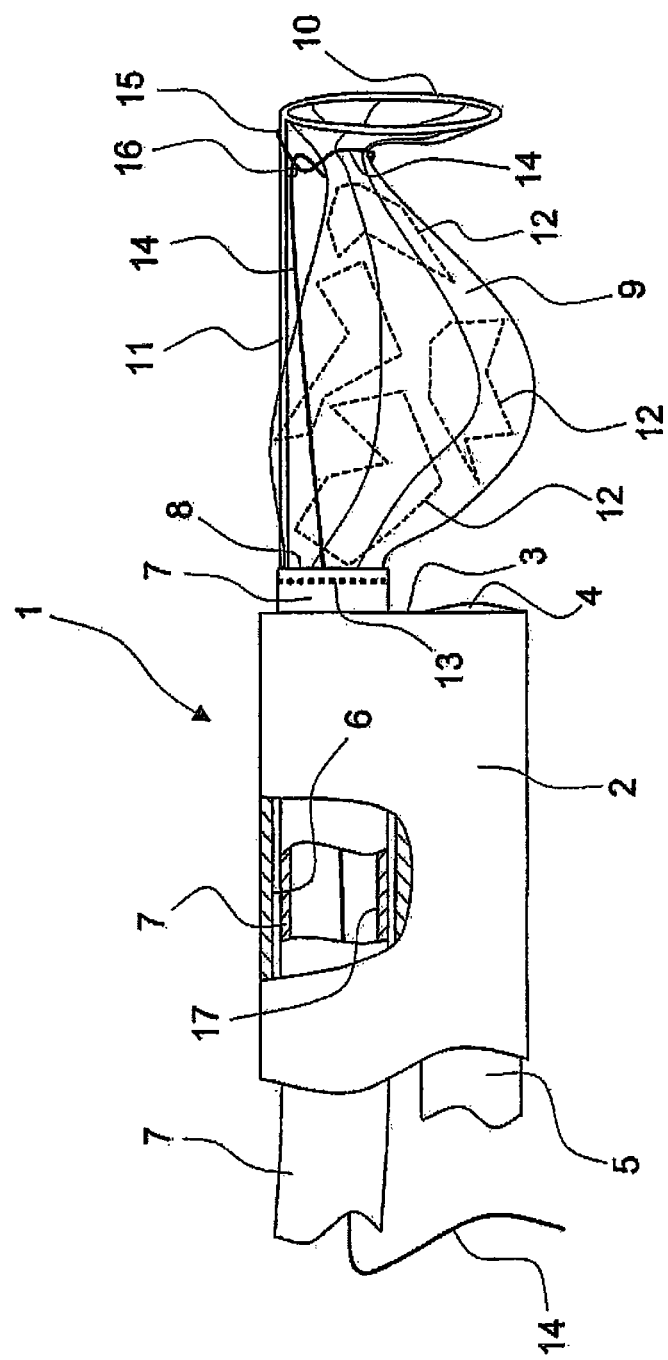

URETERAL CALCULUS SUCTION INSTRUMENT HAVING A SHAFT

CROSS-REFERENCE TO RELATED APPLICATION

The present application is based upon and claims the benefit of priority from PCT/EP2011/002465 filed on May 18, 2011, which claims benefit to DE 10 2010 024 360.4 filed on Jun. 18, 2010, the entire contents of each of which are incorporated herein by reference.

BACKGROUND

1. Field

The present invention generally relates to a ureteral calculus suction instrument, and particularly to a ureteral calculus suction instrument of the type referred to in claim 1.

2. Prior Art

Ureteroscopes serve to work in the ureter, the channel within the body which connects the kidneys to the bladder. Because this channel is very narrow, the diameter of the shaft of the ureteroscope must not be more than a maximum of 4-5 mm.

The very narrow cross-section of the shaft must accommodate the image conductor of an optical system. This exhibits at the distal end of the shaft a lens, from which an image conductor runs along the length of the shaft, consisting of rod lenses located one behind another, a light-conducting fibre bundle, or a video cable attached to a video camera.

With known ureteroscopes, a channel is arranged in the remaining very narrow cross-section, which serves as a working channel to accommodate instruments such as, for example, a lithotripter, for example in the form of a laser fibre, but which can also be used as a suction channel. The ureteroscope can therefore be used as a generic ureteral calculus suction instrument, in order to extract by suction calculus fragments produced with the lithotripter.

A disadvantage with the known generic ureteral calculus suction instruments is the suction of calculus fragments through the suction channel, which is very narrow, with a cross-section in the size range of the calculus fragments, as a result of which blockages occur due to calculus fragments becoming wedged in the suction channel. As well as this, the size of the calculus fragments which can be suctioned off is limited by the diameter of the suction channel.

SUMMARY

An object of the present invention is to improve the generic ureteral calculus suction instrument in respect of the blockage problems and the restriction on the size of the calculi which can be suctioned off.

According to the invention, a collecting container with two openings is arranged distally before the ureteral calculus suction instrument, wherein the suction channel is connected to one of the openings. In consequence, the fluid in which this operation is conducted is suctioned through the distal opening and through the collecting container. Calculus fragments which are suctioned off pass into the collecting container and can be held in this and removed with this, without them having to be moved through the suction channel. The removal of the collecting container can take place together with the shaft of the ureteral calculus suction instrument, which may be a ureteroscope, such that the full cross-section of the ureteroscope is available for the expansion of the collecting container. In this way, therefore, very large calculi or calculus fragments can be removed.

The suction channel can be formed by the working channel present in a conventional ureteroscope. The collecting container can be arranged at its distal end, before the ureteroscope, and with its proximal opening connected to the distal mouth of the working channel. Advantageously, however, the features of claim 2 are provided. In this situation, the suction channel is formed in a hose. This may serve directly as the shaft of the ureteral calculus suction instrument. The shaft may, however, also be used in the working channel of a ureteroscope, from which it can be withdrawn, such that the full cross-section of the working channel is available for a lithotripter, such as a laser fibre.

The collecting container may be secured directly to the hose, and pushed with this into the working channel of the ureteroscope. The features of claim 3 are advantageously provided for this purpose. With a flexible design of the collecting container, it can be pushed forwards, folded together, through the narrow working channel of the ureteroscope, in order then to unfold distally before the ureteroscope into the container shape. The flexibility should be carefully selected, in order to lend both the hose as well as the collecting container a certain inherent rigidity. Both require this in order not to collapse during suction.

If the collecting container is very soft, it may be difficult to hold its distal opening in a position which is favourable for the suction of calculus fragments. Accordingly, the features of claim 4 are provided. In this situation, the wall material of the collecting container can be very soft, but the distal opening is held with a support device, such that it remains open and stands in a suitable position. The support device may be, for example, a separate wire frame, to which the wall material of the collecting container is secured. The bracing can be integrated into the wall material of the collecting container. The wall material of the collecting container may also be of a suitable strength to form the support device, which advantageously, according to claim 5, is flexible. It is therefore possible for the support device to be formed with larger dimensions than the cross-section of the working channel. The support device can then be pushed through the working channel, like the collecting container, in a folded state, in order then to unfold in front of it.

Advantageously, according to claim 6, the distal opening of the collecting container can be closed. This prevents the calculi held in the collecting container from falling out again, which can happen with the high stresses imposed when the collecting container is drawn out together with the ureteroscope.

In order to prevent calculi or calculus fragments which are suctioned into the collecting container from passing into the suction channel and then blocking it, it is possible, for example, for the mouth edge of the suction channel to be somewhat reduced in diameter, such that only very small calculus fragments can pass into the suction channel, with which the risk of blockage is reduced. Such measures, however, lead to a reduction in the suction capacity, which makes the suctioning of calculus fragments more difficult. The features of claim 7 are therefore advantageously provided. A filter in the region of the entry to the suction channel, which may be formed, for example, as a relatively coarse grille with low flow resistance, keeps calculi away, such that they remain in the collecting container. By way of this measure, the blockage of the suction channel is extremely effectively prevented.

Advantageously, according to claim 8, the collecting container and the shaft are formed individually or collectively, for preference as a structural unit, as a one-off disposable article, as a result of which excellent sterility is assured.

The ureteral calculus suction instrument may exhibit as the shaft only the hose, which can also be formed as a rigid tube, in order to allow for reliable steering and control when pushed forwards into the body. Advantageously, however, according to claim 9, the ureteral calculus suction instrument is formed as a ureteroscope. This provides a range of advantages, such as, for example, the optical system provided in the ureteroscope, which allows for suction extraction to take place under visual monitoring and control.

BRIEF DESCRIPTION OF THE DRAWING

In the drawing, the invention is represented by way of example and schematically in the FIGURE, which shows a side view of the distal end region of a ureteral calculus suction instrument according to the invention in the form of an ureteroscope.

DETAILED DESCRIPTION

Represented in the FIGURE is a ureteral calculus suction instrument in the form of a ureteroscope 1, with only the distal end region of its shaft 2 represented. The shaft 2 ends distally with its distal face surface 3, in which a lens 4 of an optical system is located, which exhibits an image conductor 5 running through the shaft 2, which conveys the image acquired by the lens 4 to the proximal end of the shaft 2, in order to be observed or displayed there. The image conductor 5 can be designed as an arrangement of rod lenses or as a light-conducting fibre bundle. A camera can also be arranged at the lens 4, wherein the image conductor 5 is designed as a video cable.

In a sectional region of the shaft 2 it can be seen that a working channel 6 runs through this. In a usual arrangement this is open at both ends. In the embodiment shown, it accommodates a hose 7 with a lumen 17, which can be connected at the proximal end, not shown, to a suction device, such as a pump.

The region represented of the ureteroscope 1, when in use in accordance with the intended purpose, is arranged in the ureter or in the renal pelvis respectively, i.e. in fluid. This can be suctioned off through the hose 7 with its lumen 17 serving as a suction channel.

With the hose 7 withdrawn, a lithotripter, not shown, can be introduced through the working channel 6, i.e. an instrument for disintegrating kidney calculi lying in the ureter or in the renal pelvis respectively. The calculus fragments remaining after the disintegration must then be removed.

The lithotripter used heretofore, which was relocated through the working channel 6, may for example be designed as a shock wire of a shockwave lithotripter, or as a light conducting fibre of a laser lithotripter. After the destruction of a blocking calculus has been completed, the lithotripter is withdrawn from the working channel 6, and the hose 7 can now be pushed into the working position as shown. If suction is now imposed through the hose 7, calculus fragments could become wedged in the interior of the hose and block it. The arrangement as represented is provided in order to avoid this.

At the distal edge 8 of the hose 7, a collecting container 9 is secured with the edge of a proximal opening. A second distal opening of the collecting container 9 is secured to a ring 10, which, being carried by a rod 11, is held at a distance in front of the edge 8 of the hose 7.

With the embodiment shown, with the support device 10, 11 for holding the distal opening of the collecting container 9, the collecting container 9 can consist of very light, flexible material, as is represented in the FIGURE. It should still have a residual rigidity, however, in order not to collapse during suction and close off the flow.

The FIGURE shows that four calculus fragments 12, represented as broken line outlines, are lying in the interior of the container 9. They were aspirated through the distal opening of the container 9, defined by the ring 10. The calculus fragments 12 could, under strong suction, be suctioned into the hose 7, which is to be prevented in order not to incur blockages. For this purpose, a filter 13 is arranged close to the edge 8 in the hose 7, i.e. in the region of the transition between the hose 7 and the collecting container 9, which is formed, for example, as a grille and retains the calculus fragments 12.

Close to the distal end of the collecting container 9, i.e. adjacent to the ring 10, a loop of a thread 14 is looped around the container 9. The thread is secured to the rod 11 at 15, and, after looping around the collecting container 9, runs through a guide eye 16 on the rod 11, and from there through the hose 7 to the outside. The operator can draw on the outer end of the thread 14 in order to tighten the loop.

The collecting container 9 can thereby be closed at both ends, namely at one end by the filter 13, and at the other end by the loop of the thread 14. The collecting container 9 can now also be moved in a general manner without the calculus fragments 12 being able to escape from it.

The collecting container 9 and also the ring 10 of the support device are formed as elastically flexible, and can be laid or folded together sufficiently far as to be able to be pushed through the working channel 6 when introduced, before they can deploy into the position shown. Likewise, the collecting container 9 and the ring 10 can also be drawn in a backwards direction again, i.e. in the proximal direction, through the working channel 6. In this way, smaller calculi can be conveyed with the collecting container 9 through the working channel 6 to the outside. If larger calculus fragments or many calculus fragments are arranged in the collecting container 9, as is shown in the FIGURE, then the collecting container 9 is dawn out together with the entire ureteroscope 1, in order to remove the calculi.

The collecting container 9 can be formed in a manner other than that shown, e.g. widening in a funnel shape from the edge 8 to the ring 10, and made of relatively rigid self-supporting material, such that this material itself forms the support device. There is then no need for a separate rod 11 and a separate ring 10.

The collecting container 9 may also be secured directly at the distal end 8 of the working channel 6, such that there is no need for a separate hose 7.

Conversely, the shaft 2 of the ureteroscope 1 can also be done without, and the hose 7 itself can be used as a shaft.

The collecting container 9 can be formed as a closed film, or, for example, also from perforated material, provided that the perforations do not interfere too much with the desired proximal flow from the distal to the proximal opening of the collecting container 9, which could prevent the aspiration of calculi.

The hose 7 and the collecting container 9 are for preference formed as one-off disposable articles and are manufactured welded in sterile form.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A ureteral calculus suction instrument comprising:
a shaft, through which a suction channel runs, said suction channel being connectable to a suction device;
a collecting container with a distal opening and a proximal opening arranged distally from the shaft, of which the proximal opening is connected to a distal end of the suction channel and the distal opening is in fluid communication with the proximal opening through the collecting container such that suction from the suction device is provided at the distal end opening to suction one or more ureteral calculi into the collecting container via the distal opening; and
a closing member comprising a thread having a first end and a looped portion at a second end, the looped portion being looped around the collecting container at a position proximal to the distal opening, wherein a diameter of the looped portion decreases to close the distal opening of the collecting container when the first end is pulled proximally by a user.

2. The ureteral calculus suction instrument according to claim 1, wherein the shaft is formed as a hose.

3. The ureteral calculus suction instrument according to claim 1, wherein the collecting container is formed so as to be flexible.

4. The ureteral calculus suction instrument according to claim 1, wherein the distal opening of the collecting container is held by means of a support device.

5. The ureteral calculus suction instrument according to claim 4, wherein the support device is designed so as to be flexible.

6. The ureteral calculus suction instrument according to claim 1, further comprising a filter arranged in the region of the proximal opening of the collecting container so as to block access of the one or more ureteral calculi to the suction channel.

7. The ureteral calculus suction instrument according to claim 1, wherein one or more of the collecting container and the shaft are formed as one-off disposable articles.

8. The ureteral calculus suction instrument according to claim 1, wherein the ureteral calculus suction instrument is formed as a ureteroscope and the suction channel is arranged in a working channel of the ureteroscope.

9. The calculus suction instrument according to claim 1, wherein the collecting container has a solid wall with only the distal and proximal openings.

10. A ureteral calculus suction instrument comprising:
a shaft, through which a suction channel runs, said suction channel being connectable to a suction device;
a collecting container with a distal opening and a proximal opening arranged distally from the shaft, of which the proximal opening is connected to a distal end of the suction channel, the collecting container being a flexible film formed to define the distal and proximal openings; and
a closing member comprising a thread having a first end and a looped portion at a second end, the looped portion being looped around the collecting container at a position proximal to the distal opening, wherein a diameter of the looped portion decreases to close the distal opening of the collecting container when the first end is pulled proximally by a user.

11. The calculus suction instrument according to claim 10, wherein the film is a closed film having a solid wall with only the distal and proximal openings.

12. A medical device comprising:
a shaft, through which a suction channel runs, said suction channel being connectable to a suction device;
a collecting container with a distal opening and a proximal opening arranged distally from the shaft, of which the proximal opening is connected to a distal end of the suction channel and the distal opening is in fluid communication with the proximal opening through the collecting container such that suction from the suction device is provided at the distal end opening to suction bodily debris into the collecting container via the distal opening; and
a closing member comprising a thread having a first end and a looped portion at a second end, the looped portion being looped around the collecting container at a position proximal to the distal opening, wherein a diameter of the looped portion decreases to close the distal opening of the collecting container when the first end is pulled proximally by a user.

13. The medical device of claim 12, wherein the bodily debris is one or more ureteral calculi.

* * * * *